(12) United States Patent
Gwon et al.

(10) Patent No.: US 6,482,229 B1
(45) Date of Patent: Nov. 19, 2002

(54) ANTERIOR CHAMBER INTRAOCULAR LENS HAVING FIXATION MEMBERS ATTACHED TO THE CORNEA AND METHODS OF IMPLANTATION

(75) Inventors: Arlene Gwon, Newport Beach, CA (US); Daniel G. Brady, San Juan Capistrano, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 92 days.

(21) Appl. No.: 09/717,605

(22) Filed: Nov. 21, 2000

(51) Int. Cl.⁷ .................................................. A61F 2/16
(52) U.S. Cl. ..................... 623/6.43; 623/6.53; 623/6.36
(58) Field of Search ................................ 623/6.43, 6.44, 623/6.45, 6.46, 6.47, 6.49, 6.51–6.55, 6.56, 6.36

(56) References Cited

U.S. PATENT DOCUMENTS

| 4,134,160 A | | 1/1979 | Bayers |
| 4,502,162 A | * | 3/1985 | Gerhard et al. ............. 623/6.46 |
| 4,504,981 A | | 3/1985 | Walman |
| 4,661,109 A | | 4/1987 | White |
| 4,834,748 A | | 5/1989 | McDonald |
| 5,019,097 A | | 5/1991 | Knight et al. |
| 5,071,432 A | * | 12/1991 | Baikoff ....................... 623/6.46 |
| 5,078,740 A | | 1/1992 | Walman |
| RE34,424 E | * | 10/1993 | Walman ...................... 623/6.46 |
| 5,433,745 A | | 7/1995 | Graham et at. |
| 5,496,366 A | * | 3/1996 | Cumming ................... 623/6.46 |
| 5,766,244 A | * | 6/1998 | Binder ........................ 623/6.46 |
| 5,846,187 A | * | 12/1998 | Bayers ........................ 623/6.46 |
| 6,224,628 B1 | * | 5/2001 | Callahan et al. ............. 623/6.4 |
| 6,398,809 B1 | * | 6/2002 | Hoffmann et al. .......... 623/6.49 |
| 6,425,917 B1 | * | 7/2002 | Blake ......................... 623/6.42 |

FOREIGN PATENT DOCUMENTS

GB 0810232 3/1959

* cited by examiner

Primary Examiner—David H. Willse
Assistant Examiner—Suzette J. Jackson
(74) Attorney, Agent, or Firm—Stout, Uxa, Buyan & Mullins, LLP; Frank J. Uxa; Peter Jon Glack

(57) ABSTRACT

An intraocular lens configured to be implanted in the cornea from the posterior aspect. The lens has an optic and a pair fixation members extending outward therefrom. One of the fixation members includes a single enlarged foot, while the other fixation member has two bifurcated feet. The fixation members are sized and shaped to fix within tunnels formed in the cornea. A method of the invention includes forming tunnels in the stroma layer of the cornea, and positioning the fixation members in the tunnels. The tunnels may be formed from outside or inside the cornea. The method may include inserting the folded intraocular lens into the anterior chamber, permitting the lens to unfold, inserting the fixation member with the enlarged foot in one of the tunnels, and bending the two bifurcated feet of the other fixation member together so as to fit within the other tunnel.

12 Claims, 4 Drawing Sheets

ANTERIOR CHAMBER INTRAOCULAR LENS HAVING FIXATION MEMBERS ATTACHED TO THE CORNEA AND METHODS OF IMPLANTATION

BACKGROUND OF THE INVENTION

The present invention relates to intraocular lenses and, in particular, to an anterior chamber intraocular lens adapted to be fastened to the posterior aspect of the cornea.

Intraocular lenses (IOLs) are commonly used to modify or enhance vision. IOLs can be placed at various positions or locations within the eye. For example, IOLs can be placed in the anterior chamber (AC) of the eye, that is, the region of the eye posterior of the cornea and anterior of the iris.

IOLs may generally be classed by material. Hard or rigid IOLs are distinguished from soft IOLs that may be folded to facilitate implantation through a small incision in the cornea or sclera.

Although there are substantial advantages to placing the IOL in the anterior chamber of the eye, various complications have been reported as a result of the presence of IOLs in such anterior chambers. For example, anterior chamber IOLs have been reported to cause detrimental endothelial cell loss in the eye; pupil retraction or ovalling, which can be both cosmetically and functionally detrimental; pupillary block, which can cause glaucoma; and decentration or offsetting displacement of the IOL away from a preferred optical axis. Such complications are particularly troublesome when the anterior chamber IOL is structured to be fixated against the iridio/corneal angle, a very delicate region of the eye. One solution to this problem for acrylic lenses, which are foldable but relatively harder than silicone lenses, has been to provide enlarged feet or pods on the end of the fixation members or haptics. In this manner, a larger surface area contact reduces irritation to the iridio/corneal angle. It would be advantageous to provide anterior chamber IOLs which result in reduced incidences of one or more of these complications.

IOLs advantageously have been foldable for insertion through small incisions in eyes, particularly for insertion in the capsular bags in the posterior chambers of the eyes. Anterior chamber IOLs have a tendency to move in a relatively uncontrolled manner after implantation in the eye. Such uncontrolled movement of an IOL in the anterior chamber can detrimentally affect the iris and/or the cornea. For example, the IOL touching the cornea can result in harmful endothelial cell loss.

It would be advantageous to provide anterior chamber IOLs which have a reduced tendency to cause or do not cause one or more of: endothelial cell loss in the eye; pupil retraction or ovalling, which can be both cosmetically and functionally detrimental; pupillary block, which can cause glaucoma; and decentration or offsetting displacement of the IOL away from a preferred optical axis. Further, it would be advantageous to eliminate problems associated with IOL fixation against the delicate iridio/corneal angle.

SUMMARY OF THE INVENTION

New IOLs for implantation in eyes, in particular in anterior chambers of the eyes, have been discovered.

The present invention provides a method of implanting an intraocular lens in an eye having a cornea, an optical axis, and an anterior chamber. The method includes introducing the intraocular lens into the anterior chamber of the eye, and suspending the lens from the cornea. The intraocular lens may have at least one (and desirably two) fixation member (s) extending outward from an optic, where the method includes implanting the fixation member(s) in the cornea from the posterior aspect. Desirably, the fixation member is implanted in the stroma layer of the cornea for better support. An elongate tunnel in the cornea may be formed into which the fixation member inserts, the tunnel preferably being formed from the exterior of the eye. Where the intraocular lens has two fixation members, two incisions in the cornea are formed generally diametrically across the optical axis, and the method includes suspending the intraocular lens by positioning each of the two fixation members in a respective incision. One of the incisions may be used to introduce the intraocular lens, preferably in a deformed, e.g., folded, configuration, to the anterior chamber. A first incision may be formed from the exterior of the eye, and a second incision may be formed from the posterior aspect of the cornea.

The present invention further includes a method of implanting an intraocular lens in an eye having a cornea defining an anterior aspect and a posterior aspect, an optical axis, and an anterior chamber. The method includes forming a least two incisions in the cornea open to the anterior chamber and suspending the intraocular lens in the anterior chamber from the incisions. The incisions may be disposed generally diametrically across the optical axis, whereby the method includes positioning each of two generally diametrically oppositely-directed fixation members of the intraocular lens in a respective incision. One of the incisions may be formed from the posterior aspect, or both of the incisions may be formed from the anterior aspect. Desirably, at least one of the incisions is sized to permit introduction of the intraocular lens in a deformed insertion configuration therethrough. At least one of the incisions may have a tunnel portion that extends within the stroma layer of the cornea, preferably for about 2 mm. Furthermore, the incision having the portion that extends within the stroma layer may have a stepped configuration, with a portion opening to the posterior aspect, and an optional portion opening to the anterior aspect.

In a further embodiment, an intraocular lens, for example, an acrylic intraocular lens for corneal implantation in the anterior chamber of an eye is provided. The intraocular lens has an optic with an optical axis and an outer edge. A pair of fixation members extends outward from the optic outer edge. A first fixation member comprises an elongate, curved strut terminating in an enlarged foot, and a second fixation member comprises an elongate, curved strut bifurcated into two outer struts each terminating in a foot that is approximately the same thickness as the associated outer strut. Desirably, each of the feet is angled respect to the associated outer strut so that the feet point away from one another. The fixation members may be angled with respect to the optical axis in an anterior direction, preferably at an angle between about 15 and about 65 degrees.

Each and every feature described herein, and each and every combination of two or more of such features, is included within the scope of the present invention provided that the features included in such a combination are not mutually inconsistent.

These and other aspects and advantages of the present invention will become apparent in the following detailed description and claims, particularly when considered in conjunction with the accompanying drawings in which like parts bear like reference numerals.

DESCRIPTION OF THE PREFERRED EMBODIMENTS

Figure 1:
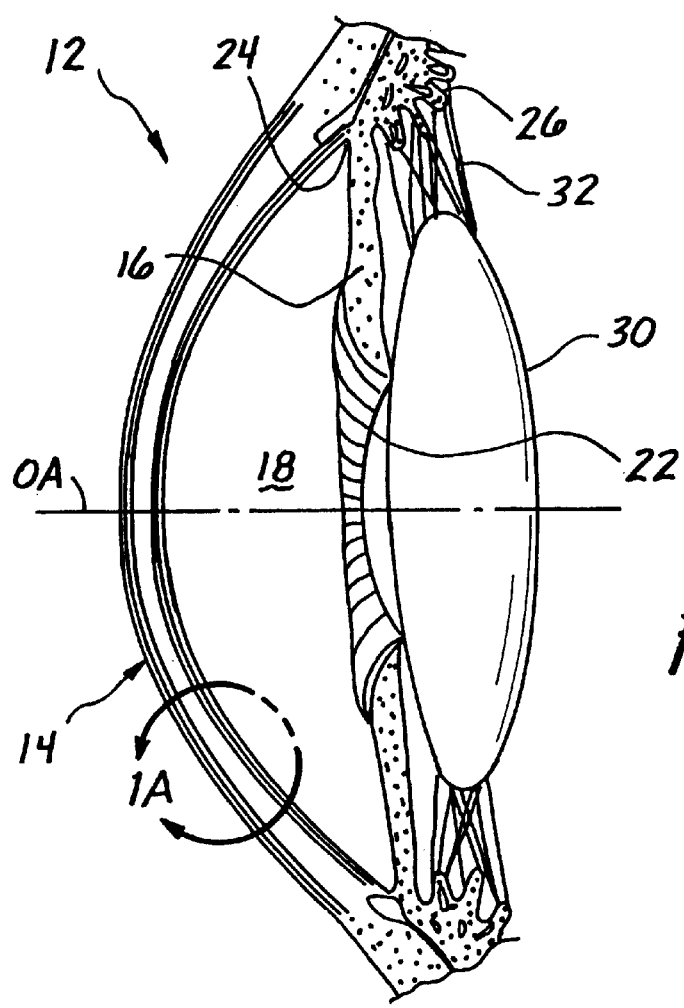
FIG. 1 is a vertical sectional view through the anterior portion of an eye, illustrating the layers of the cornea.

Referring now to FIG. 1, the eye 12 comprises a cornea 14 shown to the left or front of the eye and an annular iris 16 shown in the middle of the eye. The iris 16 divides the eye 12 into an anterior chamber 18 at the front and a posterior chamber (not shown) in back of the iris. For purpose of orientation, the directions "anterior" and "posterior" are as commonly known, i.e., forward and rearward, respectively. The iris 16 also defines the aperture or pupil 22, which is a variable opening in the middle of the iris. The posterior face of the cornea 14 and the anterior face of the iris 16 meet at the peripheral ciliary band defining an iridio-corneal angle 24. Behind the iris 16 is the ciliary process 26, which controls the movements of the natural crystalline lens 30 of the eye 12 via a plurality of fibrous zonules 32. In the human eye, an optical axis OA is generally aligned along the centers of the cornea 14, the natural lens 30 and the retina (not shown) of the eye 12.

Figure 1A:
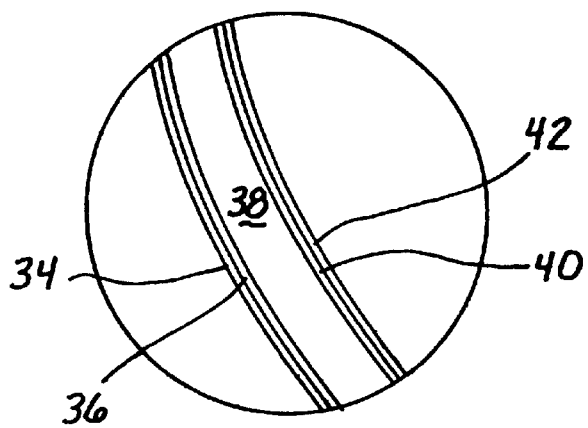
FIG. 1A is an enlarged sectional view through a portion of the cornea of FIG. 1 illustrating the various corneal layers.

With reference to FIG. 1A, the cornea 14 comprises five layers, including, from the outermost to the innermost, posterior layer, an outer layer 34 of epithelial cells, Bowman's membrane 36, the stroma 38, Descemet's membrane 40, and the endothelium 42.

Figure 2A:
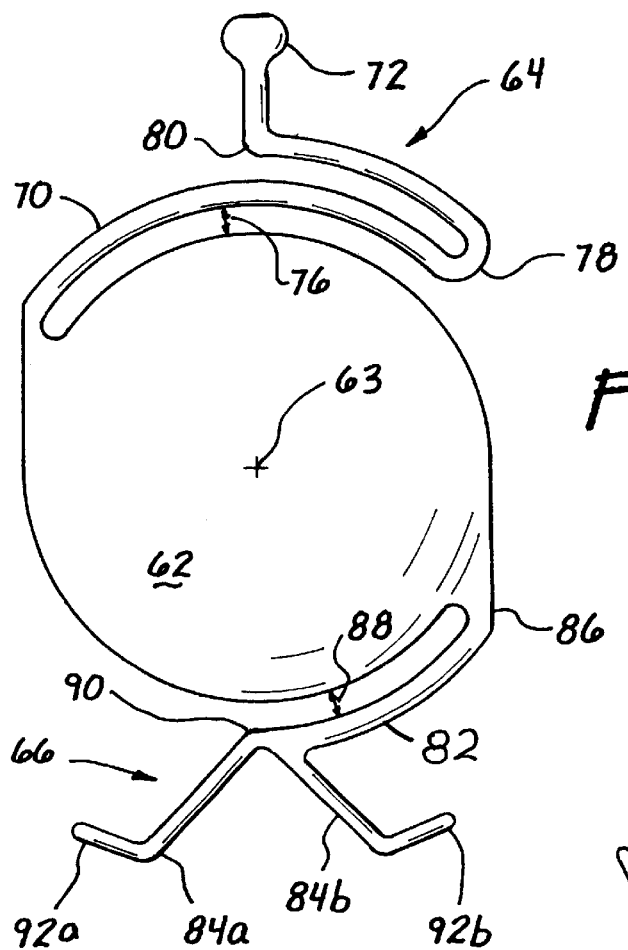
FIG. 2A is a frontal elevational view of an exemplary intraocular lens of the present invention.
Figure 2B:
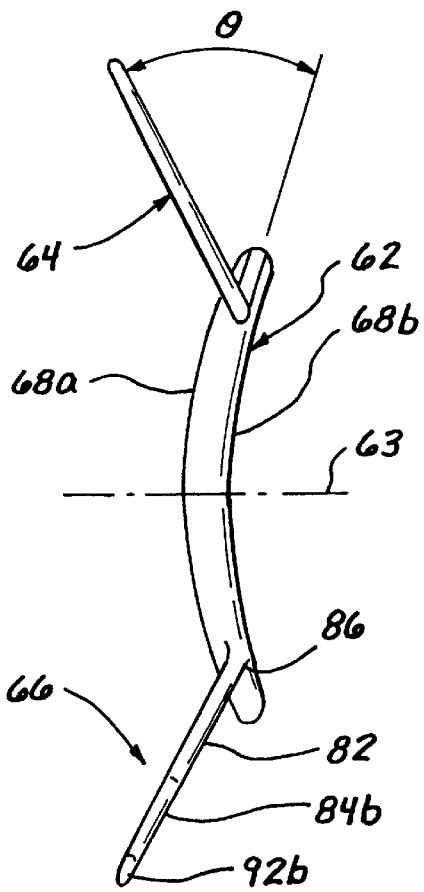
FIG. 2B is side elevational view of the intraocular lens of FIG. 2A.
Figure 4A:
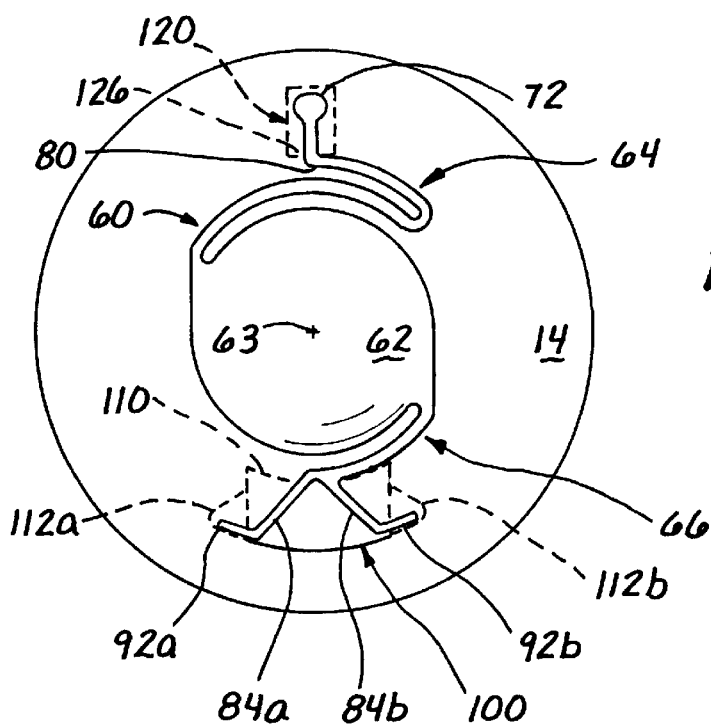
FIGS. 4A–4B are front elevational and vertical sectional views of an eye showing the placement of an exemplary intraocular lens of present invention in the posterior aspect of the cornea.

FIGS. 2A–2B illustrate an exemplary intraocular lens 60 that can be positioned in the anterior chamber 18 of the eye 12 and implanted in the posterior aspect of the cornea 14, as described below with respect to FIGS. 4A–4B. The intraocular lens 60 includes a generally circular optic 62 defining an optical axis 63 at its center, a first fixation member 64 projecting generally in one direction from the optic, and a second fixation member 66 projecting generally in the opposite direction relative to the first fixation member. The fixation members 64, 66 are sometimes known as haptics or loops. The optical axis 63 is an imaginary line that passes through the optical centers of both faces of the intraocular lens 60.

As seen in FIG. 2B, the optic 62 includes a typically convex anterior face 68a, and a typically concave posterior face 68b. The fixation members 64, 66 are coplanar or angled forwardly away from the optic 62, in the anterior direction. An angle θ is shown to indicate the degree of forward angle of each of the fixation members 64, 66. The angle θ is desirably between about 10 or about 15 and about 65 degrees.

The intraocular lens 60 may be made from a variety of materials, and the optic 62 may be the same as or a different material than the fixation members 64, 66. For example, the optic 62 and/or fixation members 64, 66 may be made from hydrophobic or hydrophilic acrylic polymeric materials, silicone polymeric materials, collagen, collagen-containing composites, polymethyl methacrylate (PMMA) and the like and mixtures thereof. Desirably, the fixation members 64, 66 are relatively stiffer with respect to the deformable, e.g., foldable, optic 62.

With reference again to FIG. 3A, the first fixation member 64 includes an elongate, curved strut 70 that attaches to the optic 62 and terminates in a single, enlarged foot 72. Using a clock-face nomenclature, with the optical axis 63 at the center, the curved strut 70 commences at a reinforced region 74 at about the 10:00 position on the outer edge of the optic 62. The strut 70 extends in a clockwise direction a small distance 76 away from and conforming to the upper edge of the optic 62 until a U-bend 78 at approximately the 2:00 position. The strut 70 then reverses in a counter-clockwise direction to a 90 degree bend 80 at the 12:00 position, the strut extending directly radially outward therefrom to the enlarged foot 72.

The second fixation member 66 includes an elongate, curved strut 82 attached the optic 62 that diverges to a pair of outer struts 84a, 84b. The curved strut 82 commences at a reinforced region 86 at about the 4:00 position on the outer edge of the optic 62 and extends in a clockwise direction a small distance 88 away from and conforming to the lower edge of the optic 62 until a three-way junction portion 90 at approximately the 6:00 position. The two outer struts 84a, 84b diverge outward by an included angle of about 90 degrees and terminate in feet 92a, 92b, each of which is angled with respect to the outer strut so that the feet point away from one another. In a particularly preferred embodiment, the two outer struts 84a, 84b have a thickness, and the feet 92a, 92b also have a thickness that is approximately the same as the struts. The advantage of such a configuration will be described below in reference to a method of implantation.

The combination of the enlarged foot 72 of the first fixation member 64 and the bifurcated feet 92a, 92b on the second fixation member 66 results in a three-point fixation of the intraocular lens 60 within the eye. More specifically, and with reference again to FIG. 2, the enlarged foot 72, and bifurcated feet 92a, 92b are implanted in the cornea 14 from the inside or posterior aspect of the cornea, and support the optic 62 along the optical axis 63.

There are a number of ways to implant fixation members of intraocular lenses into the cornea 14. Perhaps the easiest way is to create incisions from the posterior face of the cornea 14. Another solution is to create elongated tunnels within the cornea from the outside. Subsequently, the intraocular lens is inserted into the anterior chamber and the fixation members are positioned within the tunnels. In this manner, the fixation members are not directly adjacent to an incision leading to the outer face of the cornea, and thus they remain securely implanted in the eye.

Another consideration is the particular positioning of the fixation members within the corneal layers. It has been found that the middle stroma layer 38, as seen in FIGS. 1 and 2, is most suited for receiving the fixation members because of its relative thickness with respect to the other layers, and because it relatively tougher and less susceptible to wear from the inserted fixation members.

Figure 3:
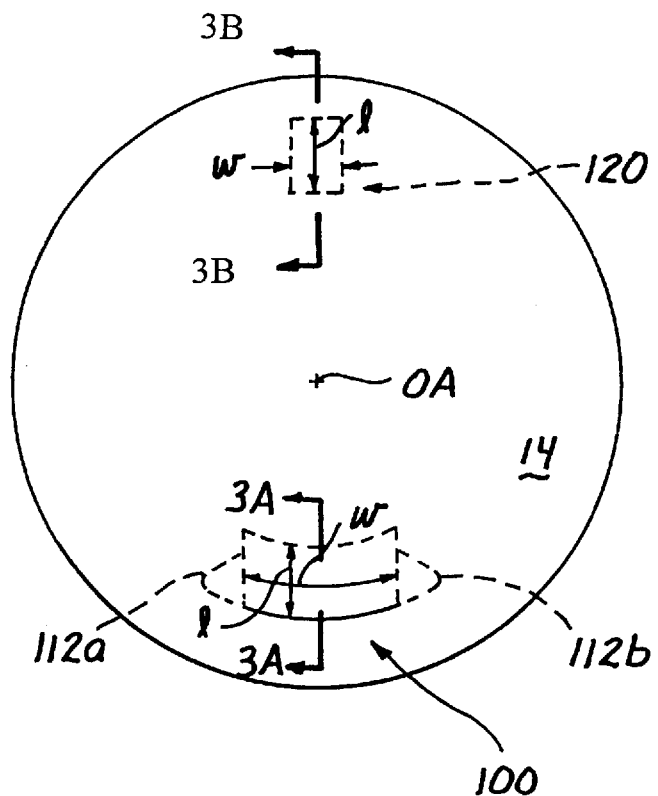
FIG. 3 is a schematic front elevational view of an eye showing the location of exemplary incisions in the cornea in a procedure for implanting an intraocular lens of the present invention.

One example of an implantation procedure of the present invention is shown schematically in FIGS. 3, 3A–3B, and 4A–4B. With reference to FIG. 3, the outer circle represents the cornea 14, as viewed from the front. In a first step, a so-called phaco incision 100 is created from the outside or anterior aspect 102 of the cornea 14 through to the inside or posterior aspect 104.

Figure 3B:
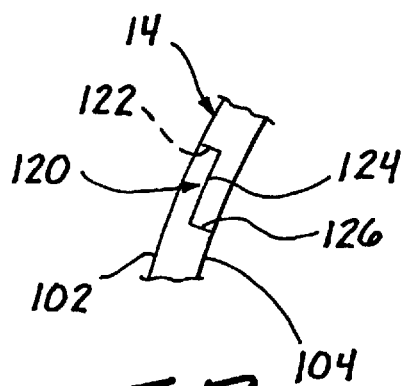
FIGS. 3A–3B are sectional views of the exemplary cornea incisions taken along respective sectional lines of FIG. 3.
Figure 3A:
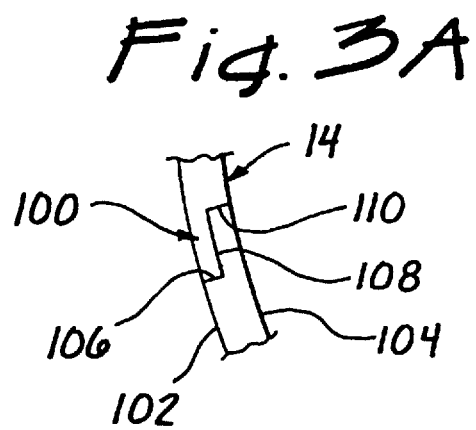

The plan view of the incision 100 is seen in FIG. 3, with a schematic sectional view shown in FIG. 3A through the cornea 14 (note that the various layers of the cornea are not illustrated for clarity). As viewed from the front view of FIG. 3, the incision 100 has a circumferential width W about the optical axis OA, a generally radial length L, and a depth through the corneal layers. As seen in FIG. 3A, the incision 100 desirably includes three sub-incisions: an entrance sub-incision 106 from the anterior aspect 102 into the stroma (not shown), a tunnel sub-incision 108 extending within the stroma, and an exit sub-incision 110 opening to the posterior aspect 104. As illustrated, the entrance sub-incision 106 is generally perpendicular with respect to the anterior aspect 102, the exit sub-incision 110 is generally perpendicular with respect to the posterior aspect 104, and the tunnel sub-incision 108 extends within the stroma and generally perpendicular to both of the other sub-incisions. In practice, due to the minute distance involved, these sub-incisions will not likely assume such idealized configurations, but will be formed in this stepped configuration nonetheless.

In an exemplary embodiment, the entrance sub-incision 106 has a circumferential width W of approximately or about 3 mm and extends through the corneal layers a depth of approximately 0.25 mm. The tunnel sub-incision 108 also has a width W of about 3 mm, and a radial length L of about 2 mm. Finally, the exit sub-incision 110 has the same circumferential width as the tunnel sub-incision 108, and extends through the corneal layers a depth of approximately 0.25 mm. The average depth of the cornea 14 is about 0.5 mm, so the tunnel sub-incision 108 desirably lies in a plane of the cornea 14 that is midway between the anterior and posterior aspects 102, 104, and within the stroma.

In one embodiment, the tunnel sub-incision 108 is widened at a pair of pockets 112a, 112b. These pockets 112a, 112b may take a variety of forms, and are illustrated as rounded incisions. The pockets 112a, 112b extend in the stroma layer in the same plane as the rest of the tunnel sub-incision 108.

A secondary incision 120 is formed in the cornea 14 at a location that is approximately diametrically opposite from the phaco incision 100. The secondary incision 120 has a width w, a length l, and a depth, as seen in the section view of FIG. 3B. The incision 120 may be formed from the outside or anterior aspect 102 of the eye, or from the inside or posterior aspect 104 using an instrument passed through the phaco incision 100. Therefore, an exit sub-incision 122 is shown in dashed line extending generally perpendicular from the anterior aspect 102. A tunnel sub-incision 124 extends generally perpendicularly through the stroma layer from the exit sub-incision 122, and leads to an entrance sub-incision 126 opening generally perpendicularly to the posterior aspect 104. The tunnel sub-incision 124 extends generally radially, such that the exit sub-incision 122 is located radially outward from the entrance sub-incision 126. As before, these sub-incisions are shown as idealized, and likely will not have such sharp and well-defined intersections.

In an exemplary embodiment, the width w of the secondary incision 120 is about 1 mm, while the length l is about two mm. The depth of the stepped sub-incisions are as described above with respect to the phaco incision 100, with the tunnel sub-incision 124 being generally located in the stroma and in a plane that is midway between the anterior aspect 102 and posterior aspect 104.

The phaco incision 100 is sized to permit introduction of the intraocular lens 60 of the present invention to the anterior chamber. Specifically, the incision 100 is sized to permit the intraocular lens 60 to pass therethrough in a folded configuration.

A method of implanting the intraocular lens 60 into an eye 12 will now be described with respect to FIGS. 4A–4B. Various techniques instruments are known for incising the cornea 14, and for a introducing and manipulating intraocular lenses within the anterior chamber 18 (FIG. 1) of the eye. For example, various diamond keratomes or blades may be used to form the incisions 100, 120, and a conventional Bartell type intraocular lens folding system used to introduce the intraocular lens 60 through the phaco incision 100. Manipulation of the intraocular lens 60, and in particular the fixation members 64, 66 may be accomplished using forceps or other such fine grabbing tools. Description of these various implements will not be included herein, as they are well-known by those of skill in the art.

The first step in implantation comprises the formation of the phaco incision 100 from the outside or anterior aspect of the eye. As described above, the incision 100 is desirably stepped as indicated in FIG. 3A, with a relatively large tunnel sub-incision 108 being formed parallel to the corneal layers, and within the stroma. Subsequently, the secondary incision 120 is formed, either from the outside or anterior aspect of the eye, or from the inside or posterior aspect. In the latter instance, a suitable keratome may be inserted through the phaco incision 100 to form just the entrance sub-incision 126 and tunnel sub-incision 124, as indicated in FIG. 3B. Alternatively, the secondary incision 120 may be formed from the outside, with the three sub-incisions 122, 124, and 126 being formed in sequence.

The intraocular lens 60 can then be introduced to the anterior chamber 18 through the phaco incision 100. After unfolding, the intraocular lens 60 is desirably in an orientation as seen in FIG. 4A, or is manipulated into that orientation, with the first fixation members 64 extending generally toward the secondary incision 120, and the second fixation members 66 extending generally toward the phaco incision 100.

The first fixation members 64 is then inserted into the secondary incision 120 by passage of the enlarged foot 72 through the entrance sub-incision 126 and into the tunnel sub-incision 124 (see FIG. 3B). This relative arrangement seen in FIG. 4A. The radial length 1 of the tunnel sub-incision 126 is approximately the same as the length of the radial portion of the strut 70 between the 90° bend 80 and the enlarged foot 72. In this manner, the 90° bend 80 is positioned within the anterior chamber 18, closely adjacent to the entrance sub-incision 126.

Because of the flexibility of the fixation members 64, 66, the intraocular lens 60 can be manipulated to implant the second fixation member 66 into the phaco incision 100. In a preferred embodiment, the spacing between the feet 92a, 92b is slightly larger than the width W of the incision 100. Therefore, the diverging outer struts 84a, 84b are first bent inward toward one another so that the feet 92a, 92b can pass through the exit sub-incision 110. After proper positioning of the second fixation member 66, with the three-way junction portion 90 remaining within the anterior chamber 18 just adjacent the exit sub-incision 110, the diverging outer struts 84a, 84b are released such that the feet 92a, 92b spring outward to the sides of the tunnel sub-incision 108.

As mentioned above, the optional pockets 112a, 112b may be provided to receive the feet 92a, 92b. Alternatively, the feet 92a, 92b may contact the sides of the tunnel sub-incision 108, such that the resilient bias of the struts 84a, 84b holds the fixation member 66 in place. Furthermore, because the feet 92a, 92b are not enlarged as are prior art acrylic lens fixation members for use in the iridio/corneal angle, they may become embedded in the stroma layer on the sides of the tunnel-incision 108. This anchoring effect helps prevent movement of the intraocular lens 60 within the cornea 14. In any event, the intraocular lens 60 is positioned as seen in FIG. 4A, with the optic 62 in the desirable centered position.

Figure 4B:
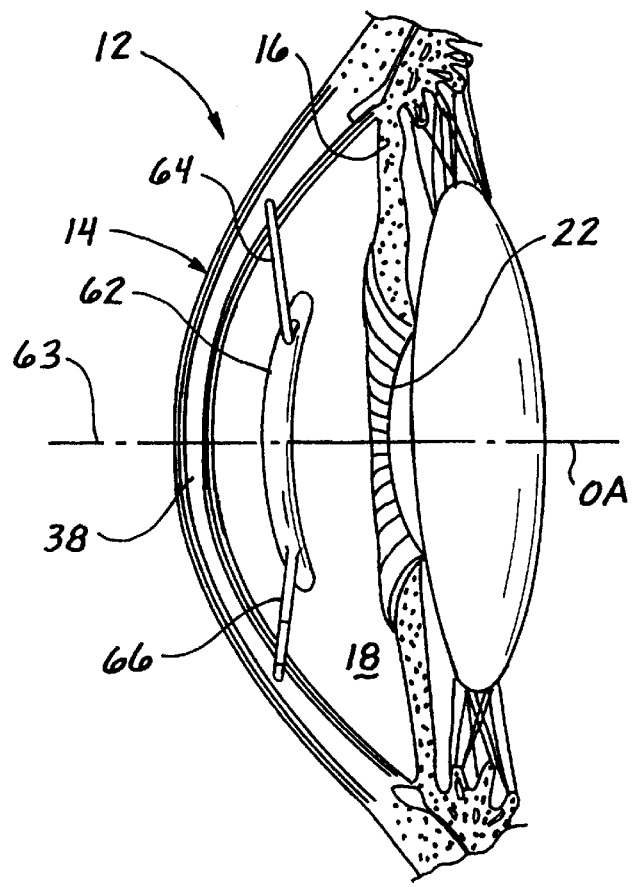

FIG. 4B shows the exemplary intraocular lens 60 of the present invention positioned in the anterior chamber 18 of the eye 12, and desirably centered along the optical axis OA for focusing light at or near the retina (not shown). Desirably, the optical axis 63 of the intraocular lens 60 coincides with the optical axis OA of the natural eye. As mentioned above, the fixation members 64, 66 extend directly radially outward or outward and forward from the typically circular optic 62 and are implanted in the cornea 14 from the inside, or posterior aspect of the cornea. The ends of the fixation members 64, 66 reside within the stroma 38, and in particular within the tunnel sub-incisions as described above. The optic 62 is thus positioned and suspended by the fixation members 64, 66 so as not to touch the cornea, which might result in harmful endothelial cell loss.

In one embodiment, as shown, the struts 84a, 84b are divergent to an extent that they provide good balance for the intraocular lens 60 when implanted in the cornea. That is, the struts 84a, 84b and feet 92a, 92b are desirably centered about a vertical plane intersecting the optical axis OA, and thus support approximately the same amount of weight of the lens. Therefore, in combination with the implantation of the first fixation member 64, the second fixation member 66 helps prevent movement of the lens in the anterior chamber.

While this invention has been described with respect to various specific examples and embodiments, it is to be understood that the invention is not limited thereto and that it can be variously practiced within the scope of the following claims. For example, although only two fixation members are shown, there may be three or more. Alternatively, only one of the disclosed fixation members may be used in combination with one or more other types of fixation member.

What is claimed is:

1. An intraocular lens for corneal implantation in the anterior chamber of an eye, comprising:
    an optic having an optical axis and an outer edge; and
    at least a pair of fixation members extending outward from the optic outer edge, wherein a first fixation member comprises an elongate, curved strut terminating in an enlarged foot, and wherein a second fixation member comprises an elongate, curved strut bifurcated into two outer struts each terminating in a foot that is approximately the same thickness as the associated outer strut, and
    wherein at least the fixation members are made of an acrylic polymeric material.

2. The intraocular lens as in claim 1, wherein, as viewed from the front and using a clock perspective centered about the optical axis, the elongate, curved strut of the first fixation member attaches to the optic at a reinforced region at about a 10:00 position on the outer edge of the optic, and extends in a clockwise direction a small distance away from and conforming to the outer edge of the optic until a U-bend at approximately the 2:00 position, the strut then reverses in a counter-clockwise direction to a 90 degree bend at the 12:00 position and continues directly radially outward therefrom to the enlarged foot.

3. The intraocular lens as in claim 2, wherein, as viewed from the front and using a clock perspective centered about the optical axis, the elongate, curved strut of the second fixation member attaches to the optic at a reinforced region at about the 4:00 position on the outer edge of the optic and extends in a clockwise direction a small distance away from and conforming to the outer edge of the optic until a three-way junction portion at approximately the 6:00 position, the strut then continues in the two outer struts diverging outward from the junction portion and each terminating in one of the feet.

4. The intraocular lens as in claim 1, wherein, as viewed from the front and using a clock perspective centered about the optical axis, the elongate, curved strut of the second fixation member attaches to the optic at a reinforced region at about the 4:00 position on the outer edge of the optic and extends in a clockwise direction a small distance away from and conforming to the outer edge of the optic until a three-way junction portion at approximately the 6:00 position, the strut then continues in the two outer struts diverging outward from the junction portion and each terminating in one of the feet.

5. The intraocular lens as in claim 4, wherein each of the feet is angled with respect to the associated outer strut so that the feet point away from one another.

6. The intraocular lens as in claim 1, wherein each of the pair of fixation members is angled with respect to the optical axis in an anterior direction.

7. The intraocular lens as in claim 6, wherein the angle is between about 15 and about 65 degrees.

8. The intraocular lens as in claim 1 wherein both the optic and fixation members are made of an acrylic polymeric material.

9. An intraocular lens for corneal implantation in the anterior chamber of an eye, comprising:
    an optic having an optical axis and an outer edge; and
    at least a pair of fixation members extending outward from the optic outer edge, wherein each of the pair of fixation members is angled with respect to the optical axis in an anterior direction, the intraocular lens being adapted for placement of the optic in the anterior chamber of the eye.

10. The intraocular lens as in claim 1, wherein the angle of the fixation members with respect to the optical axis is between about 15 and about 65 degrees.

11. The intraocular lens as in claim 9 wherein at least one of the fixation members comprises an elongate, curved strut bifurcated into two outer struts each terminating in a foot that is approximately the same thickness as the associated outer strut.

12. The intraocular lens as in claim 11 wherein at least the fixation member having the curved strut bifurcated into two outer struts is made of an acrylic polymeric material.

* * * * *

UNITED STATES PATENT AND TRADEMARK OFFICE
CERTIFICATE OF CORRECTION

PATENT NO.    : 6,482,229 B1                                        Page 1 of 1
DATED         : November 19, 2002
INVENTOR(S)   : Gwon et al.

It is certified that error appears in the above-identified patent and that said Letters Patent is hereby corrected as shown below:

Title page,
Item [74], *Attorney, Agent, or Firm,* "Peter Jon Glack" should read
-- Peter Jon Gluck --.

Column 8,
Line 51, "claim 1" should read -- claim 9 --.

Signed and Sealed this

Fifth Day of August, 2003

JAMES E. ROGAN
*Director of the United States Patent and Trademark Office*